US012789454B2

(12) United States Patent
Rodriguez Santiago et al.

(10) Patent No.: US 12,789,454 B2
(45) Date of Patent: Nov. 10, 2026

(54) BUILD-PLATE USED IN FORMING DEVICES AND LOCATING FEATURES FORMED ON THE BUILD-PLATE TO FACILITATE USE OF ADDITIVE AND SUBTRACTIVE MANUFACTURING PROCESSES AND METHOD FOR USE THEREOF

(71) Applicant: Warsaw Orthopedic, Inc., Warsaw, IN (US)

(72) Inventors: Dawin Rodriguez Santiago, Hernando, MS (US); Keith E. Miller, Germantown, TN (US); Matthew D. May, Collierville, TN (US); Dale A. Tempco, Germantown, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 635 days.

(21) Appl. No.: 18/112,912

(22) Filed: Feb. 22, 2023

(65) Prior Publication Data

US 2023/0211555 A1 Jul. 6, 2023

Related U.S. Application Data

(62) Division of application No. 16/658,193, filed on Oct. 21, 2019, now Pat. No. 11,602,893.

(51) Int. Cl.
*B29C 64/245* (2017.01)
*A61F 2/30* (2006.01)
(Continued)

(52) U.S. Cl.
CPC .......... *B29C 64/245* (2017.08); *A61F 2/3094* (2013.01); *A61F 2/447* (2013.01); (Continued)

(58) Field of Classification Search
CPC ...... B29C 64/245; B29C 64/393; B33Y 10/00
See application file for complete search history.

(56) References Cited

U.S. PATENT DOCUMENTS

| | | | |
|---|---|---|---|
| 8,021,138 | B2 | 9/2011 | Green |
| 8,994,592 | B2 | 3/2015 | Scott et al. |

(Continued)

FOREIGN PATENT DOCUMENTS

| | | |
|---|---|---|
| CN | 205929449 | 2/2017 |
| CN | 108723373 | 11/2018 |

(Continued)

OTHER PUBLICATIONS

International Search Report and Written Opinion dated Feb. 9, 2021 from International Application No. PCT/US2020/056276.

(Continued)

*Primary Examiner* — Larry W Thrower
(74) *Attorney, Agent, or Firm* — FOX ROTHSCHILD LLP

(57) ABSTRACT

A build-plate with integrally-formed spinal implant constructs and a method used in forming spinal implant constructs on the build-plate and machining the spinal implant constructs formed on the build-plate to manufacture spinal implants is provided. The spinal implant constructs can be formed via additive manufacturing processes by adding material to an upper surface of the build-plate, and then the spinal implant constructs can be subjected to subtractive manufacturing processes to form the spinal implants.

7 Claims, 6 Drawing Sheets

(51) Int. Cl.

| | |
|---|---|
| ***A61F 2/44*** | (2006.01) |
| ***B29C 64/393*** | (2017.01) |
| ***B33Y 10/00*** | (2015.01) |
| ***B33Y 30/00*** | (2015.01) |
| ***B33Y 50/02*** | (2015.01) |
| *B29L 31/00* | (2006.01) |

(52) U.S. Cl.
CPC ............ *B29C 64/393* (2017.08); *B33Y 10/00* (2014.12); *B33Y 30/00* (2014.12); *B33Y 50/02* (2014.12); *A61F 2002/30985* (2013.01); *B29L 2031/7532* (2013.01)

(56) References Cited

U.S. PATENT DOCUMENTS

| | | | |
|---|---|---|---|
| 9,597,730 | B2 | 3/2017 | Mironets et al. |
| 9,688,023 | B2 | 6/2017 | Dean et al. |
| 9,767,224 | B2 | 9/2017 | Chou et al. |
| 9,849,631 | B1 | 12/2017 | Goss et al. |
| 9,956,612 | B1 | 5/2018 | Redding et al. |
| 10,000,011 | B1 | 6/2018 | Mark |
| 10,010,936 | B2 | 7/2018 | Chou et al. |
| 10,011,469 | B2 | 7/2018 | Craft et al. |
| 10,022,794 | B1 | 7/2018 | Redding et al. |
| 10,022,795 | B1 | 7/2018 | Redding et al. |
| 10,029,307 | B2 | 7/2018 | Shea et al. |
| 10,035,298 | B2 | 7/2018 | Mark |
| 10,040,241 | B2 | 8/2018 | Mark |
| 10,040,242 | B2 | 8/2018 | Mark |
| 10,052,815 | B2 | 8/2018 | Mark |
| 10,406,759 | B2 | 9/2019 | Loeffler et al. |
| 2014/0065194 | A1 | 3/2014 | Yoo et al. |
| 2015/0061170 | A1 | 3/2015 | Engal et al. |
| 2016/0031010 | A1 | 2/2016 | O'Neill et al. |
| 2016/0144428 | A1 | 5/2016 | Mironets et al. |
| 2016/0213485 | A1 | 7/2016 | Schaufler et al. |
| 2017/0143495 | A1 | 5/2017 | Dunn et al. |
| 2018/0153661 | A1 | 6/2018 | Beeby et al. |
| 2018/0326493 | A1 | 11/2018 | Gallagher et al. |
| 2018/0326668 | A1 | 11/2018 | Walker et al. |
| 2018/0349519 | A1* | 12/2018 | Schroeder ............... G06F 30/23 |
| 2020/0192332 | A1* | 6/2020 | Jacobs ............... G05B 19/4099 |
| 2020/0238447 | A1* | 7/2020 | Fedyk .................. B23K 26/342 |

FOREIGN PATENT DOCUMENTS

| | | |
|---|---|---|
| EP | 3417961 | 12/2018 |
| FR | 3055564 | 3/2018 |

OTHER PUBLICATIONS

Extended European Search Report dated Aug. 9, 2023 in European Application No. 20878825.7.

Elena Provaggi et al: of 3D printing in management of severe spinal conditions, Proceedings of the Institution of Mechanical Engineers. of Engineering Medicince. Part H., vol. No. 6, Jun. 22, 2017 (Jun. 22, 2017), pp. 471-486, XP055406664, GB ISSN: 0954-4119, DOI: 10.1177/0954411916667761.

* cited by examiner

BUILD-PLATE USED IN FORMING DEVICES AND LOCATING FEATURES FORMED ON THE BUILD-PLATE TO FACILITATE USE OF ADDITIVE AND SUBTRACTIVE MANUFACTURING PROCESSES AND METHOD FOR USE THEREOF

The present application is a divisional of U.S. application Ser. No. 16/658,193, Oct. 21, 2019, which is hereby incorporated by reference herein in its entirety.

FIELD

Field

The present technology is generally related to a build-plate used in forming devices such as spinal implants and locating features formed on the build-plate to facilitate use of additive and subtractive manufacturing processes.

Background

Spinal implants have been formed using additive and subtractive machining processes. For example, single spinal implants have been formed by additive manufacturing processes, and thereafter, such spinal implants having been subjected to subtractive manufacturing process. The additive manufacturing processes, as their name suggests, adds material to form the spinal implants. And the subtractive manufacturing processes, as their name suggests, subtracts material to form the spinal implants. As such, the additive manufacturing processes can be used in generally forming the shapes of the spinal implants as spinal implant constructs, and the subtractive manufacturing processes can be used in refining the shapes of the spinal implants. A build-plate can be used to facilitate formation of the spinal implant constructs using the additive manufacturing processes, and then the build-plate with the spinal implant constructs can be subjected to the subtractive manufacturing processes to form the of the spinal implants. However, difficulties arise in properly positioning the build-plate for the additive manufacturing processes and then the subtractive manufacturing processes. Inaccuracies can arise in positioning the build-plate that can adversely affect the additive manufacturing processes and/or the subtractive manufacturing process. Therefore, there is a need for features and methods for using the features that afford accurate positioning of the build-plate for the additive manufacturing processes and/or the subtractive manufacturing processes.

SUMMARY

The techniques of this disclosure generally relate to a build-plate used in forming devices and locating features formed on the build-plate to facilitate use of additive and subtractive manufacturing processes.

In one aspect, the present disclosure provides a method of using a build-plate including providing a build-plate having an upper surface, a lower surface, a first locating feature, and a second locating feature; providing an additive manufacturing platform including a table-top and/or a spacer, one of the table-top and the spacer including an upper surface and a third locating feature; positioning the build-plate on the upper surface of the one of the table-top and the spacer, and engaging the second locating feature and the third locating feature; forming on the upper surface of the build-plate a set of orthopedic implant constructs via an additive manufacturing process performed by the additive manufacturing platform; measuring a position of the set of the orthopedic implant constructs relative to the first locating feature; determining a correction factor based on the measured position of the set of orthopedic implant constructs; and using the correction factor for relative adjustment of the build-plate relative to a subtractive manufacturing platform to facilitate accurate positioning for performance of a subtractive manufacturing process on each of the orthopedic implant constructs.

In another aspect, the disclosure provides a method of using a build-plate including providing a build-plate having an upper surface, a lower surface, and a first locating feature; providing an additive manufacturing platform including a table-top and/or a spacer, one of the table-top and the spacer including an upper surface and a second locating feature; positioning the build-plate on the upper surface of the one of the table-top and the spacer, and engaging the first locating feature and the second locating feature; forming on the upper surface of the build-plate a third locating feature and a set of orthopedic implant constructs via an additive manufacturing process performed by the additive manufacturing platform, locations of the third locating feature and the set of the orthopedic implant constructs being known with respect to one another; and using the third locating feature for relative adjustment of the build-plate relative to a subtractive manufacturing platform to facilitate accurate positioning for performance of a subtractive manufacturing process on each of the orthopedic implant constructs.

In yet another aspect, the disclosure provides a method of using a build-plate including providing a build-plate having an upper surface and a lower surface; providing an additive manufacturing platform including a table-top and/or a spacer, one of the table-top and the spacer including an upper surface; positioning the build-plate on the upper surface of the one of the table-top and the spacer; forming on the upper surface of the build-plate a first locating feature via an additive manufacturing process performed by the additive manufacturing platform; measuring a position of the first locating feature and adjusting a positon of the build-plate relative to the additive manufacturing platform to account for the position of the first locating feature; after adjustment of the build-plate relative to the additive manufacturing platform, forming on the upper surface of the build-plate a set of orthopedic implant constructs via the additive manufacturing process performed by the additive manufacturing platform; and using the measured position of the first locating feature for relative adjustment of the build-plate relative to a subtractive manufacturing platform to facilitate accurate positioning for performance of the subtractive manufacturing process on each of the orthopedic implant constructs.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
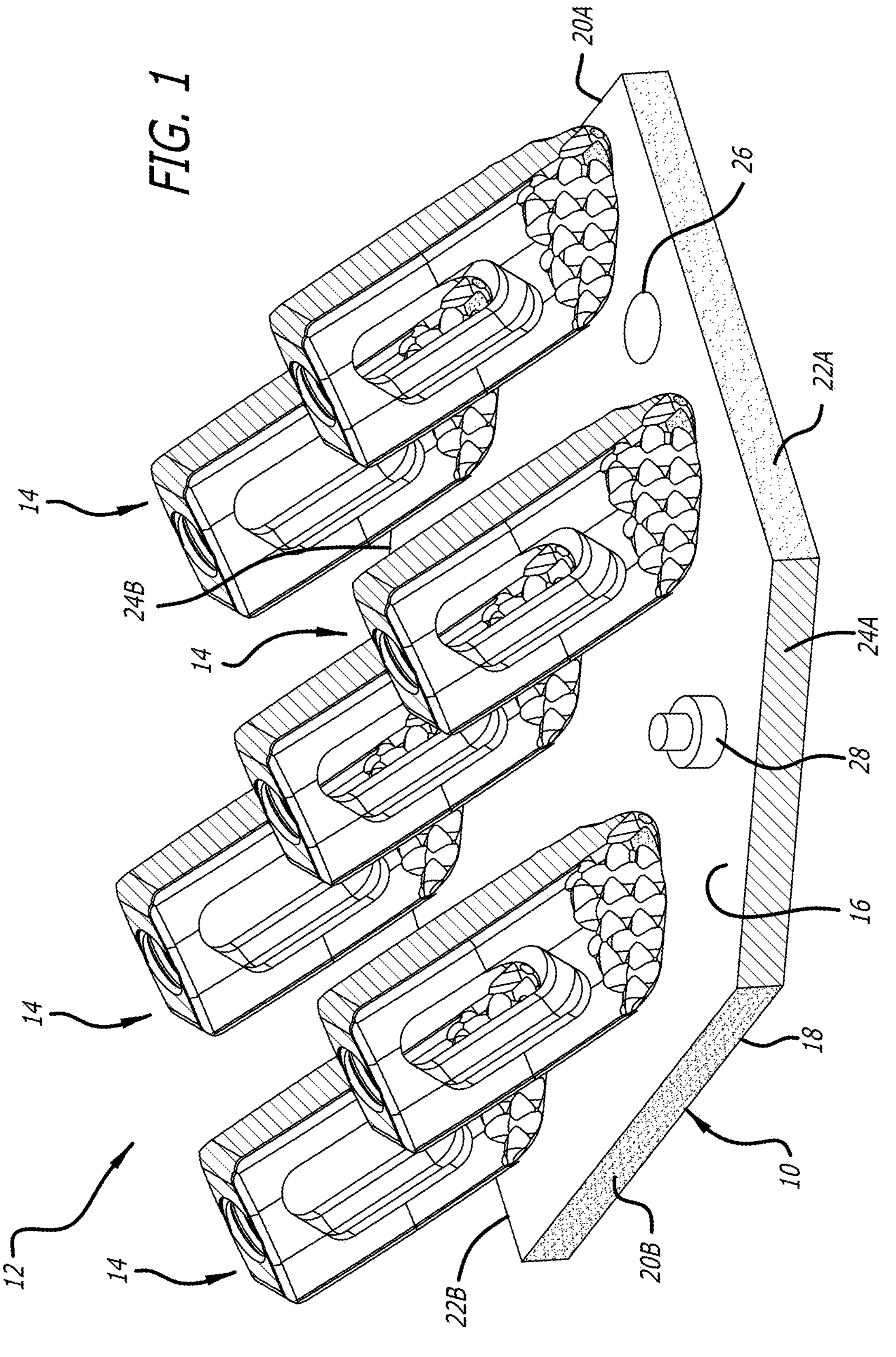
FIG. 1 is a top, side, perspective view that illustrates a build-plate with various spinal implant constructs formed on the build-plate and two locating features provided on and in an upper surface of the build-plate.
Figure 2:
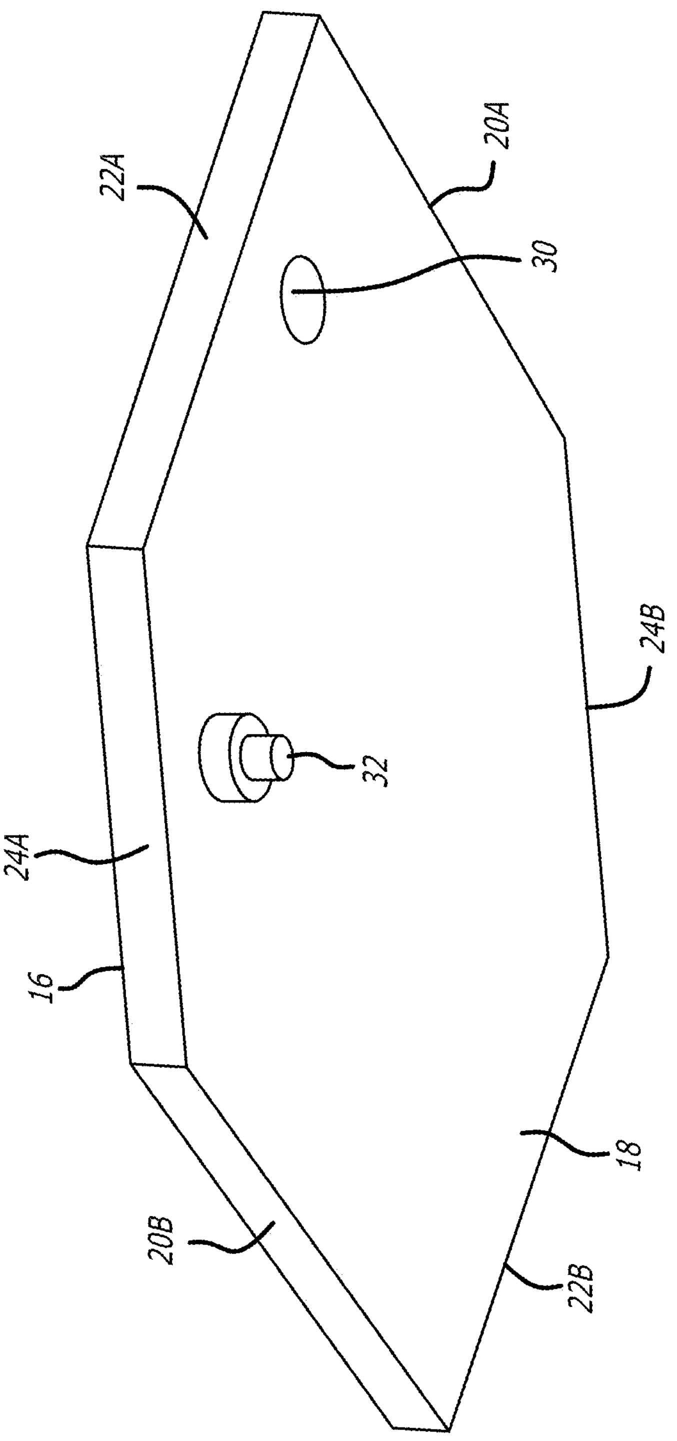
FIG. 2 is a bottom, side, perspective view that illustrates the build-plate of FIG. 1 with two locating features provided on and in a lower surface of the build-plate.
Figure 3:
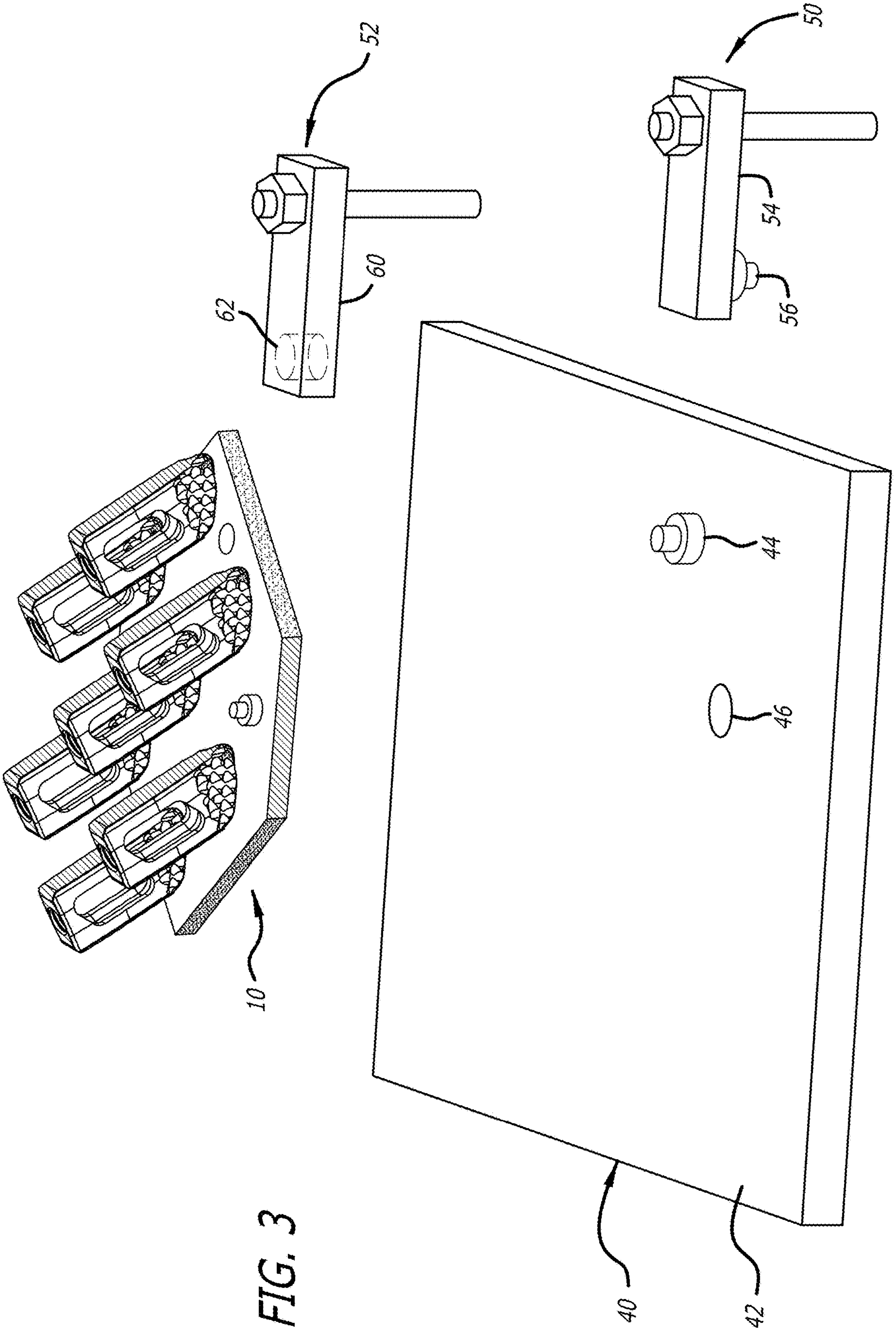
FIG. 3 is a top, side, perspective view that illustrates a table-top or spacer for use with an additive manufacturing platform, the build-plate of FIG. 1 being positioned relative to the table-top/spacer, and two clamping arms used to hold the build-plate in position relative to the table-top/spacer.
Figure 4:
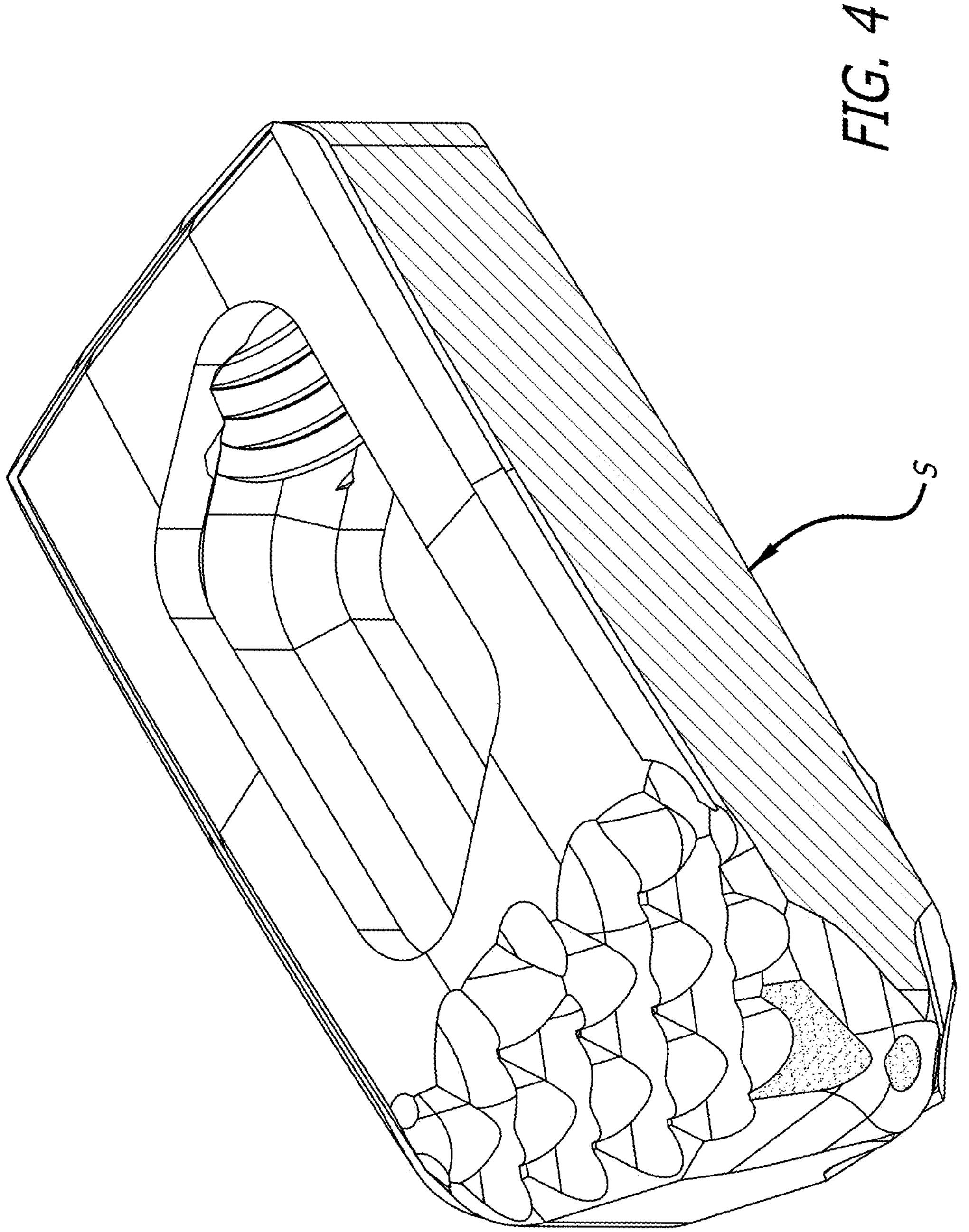
FIG. 4 is a top, side, perspective view that illustrates a spinal implant formed from one of the spinal implant constructs of FIG. 1.
Figure 5:
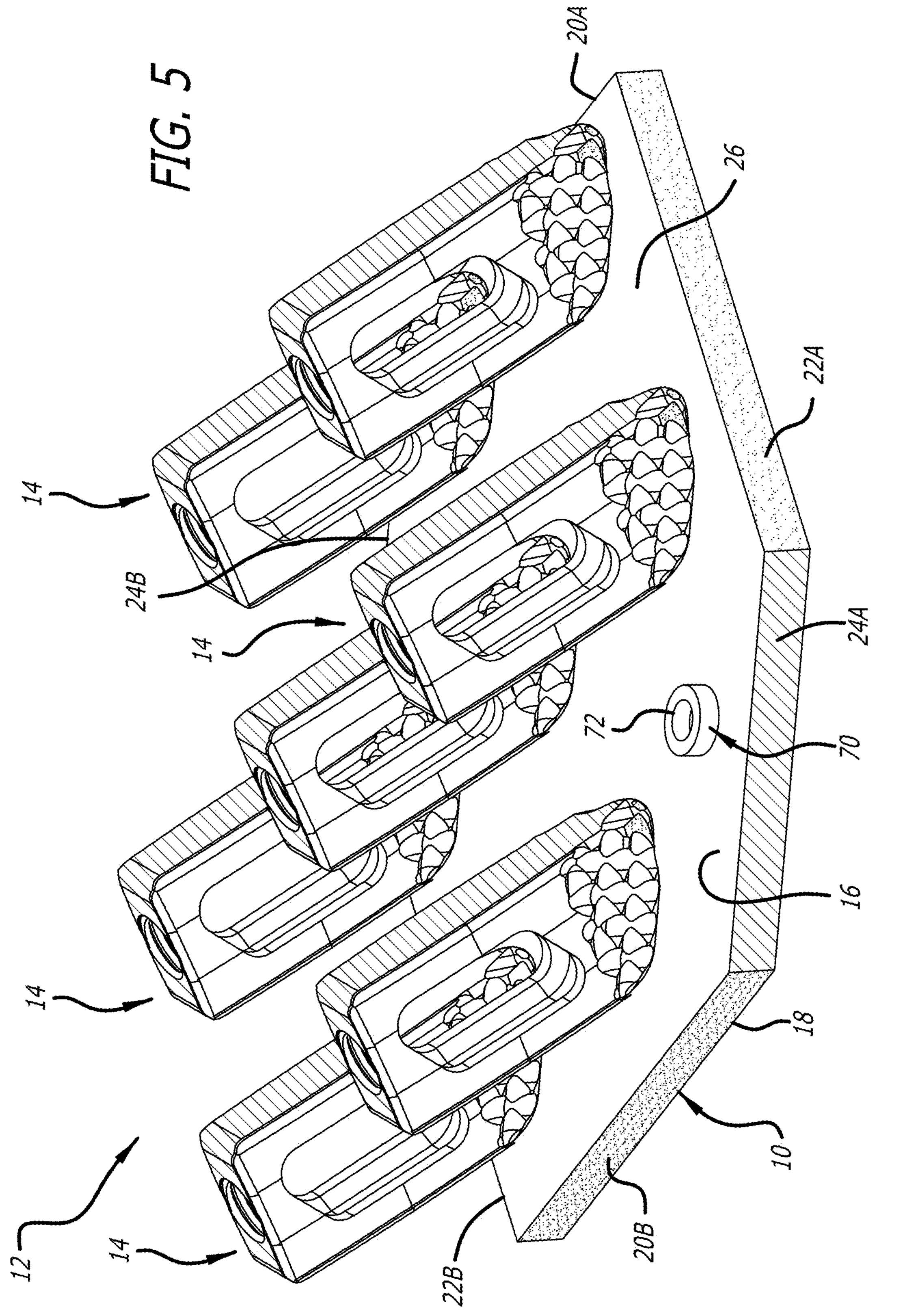
FIG. 5 is a top, side, perspective view that illustrates a build-plate with various spinal implant constructs formed the build-plate and a locating feature provided on an upper surface of the build-plate.

Additive manufacturing (or machining) processes such as, for example, 3D printing can be used in forming various devices on an additive build-plate generally indicated by the numeral 10 in FIGS. 1-3 and 5. As depicted in FIGS. 1, 3, and 5, the various devices can be a set 12 of constructs 14. The build-plate 10 and the constructs 14 can be such as those disclosed in U.S. Ser. No. 16/523,079, which is hereby incorporated by reference in its entirety. The constructs 14 can be any parts or pieces that can be formed on the build-plate 10 using additive manufacturing processes. For example, the constructs 14 can be orthopedic implant constructs used to form orthopedic implants. More specifically, the orthopedic implant constructs 14 formed on the build-plate 10 can be spinal implant constructs 14 used to form spinal implants S (FIG. 4).

The build-plate 10 is used to afford formation of the set 12 of the spinal implant constructs 14 on the build-plate 10 via the additive manufacturing processes. As discussed below, the spinal implant constructs 14 are formed on a surface of the build-plate 10 such that, after formation of the spinal implant constructs 14, the spinal implant constructs 14 can be further manufactured using additional manufacturing processes to complete manufacture of the spinal implants S.

Such additional manufacturing processes can be used to change the geometry or the surfaces of the spinal implant constructs 14, and the additional manufacturing processes can include subtractive manufacturing (or machining) processes. As such, the build-plate 10 with the spinal implant constructs 14 can serve as a unitary workpiece facilitating additional manufacturing processes (such as the subtractive manufacturing processes) applied thereto to manufacture the spinal implants S. The build-plate 10 can be used to facilitate formation of the set 12 of the spinal implant constructs 14 using the additive manufacturing processes, and then the build-plate 10 with the set 12 of the spinal implant constructs 14 can be subjected to the subtractive manufacturing processes to form the of the spinal implants S. The build-plate 10 with the spinal implant constructs 14 can be used to facilitate repeatable, batch processing for volume manufacturing of the spinal implants S using additive manufacturing processes and subtractive manufacturing processes.

As discussed below, the build-plate 10 can include physical locating features for accurately positioning the build-plate 10 to facilitate application of singular or pluralities of the additive machining processes to the build-plate 10 performed by an additive manufacturing platform or platforms and the subtractive manufacturing processes performed by a subtractive manufacturing platform or platforms. The additive manufacturing platforms and the subtractive manufacturing platforms include tools for performing the aforementioned processes. And the additive manufacturing processes, can include, but are not limited to 3D printing, and the subtractive manufacturing processes can include, but are not limited to, electrical discharge machining (EDM), CNC machining (turning, drilling boring, milling, reaming, etc.), laser cutting/etching, and water jet cutting/etching.

To illustrate, the spinal implant constructs 14 can each be formed via the additive manufacturing process or processes by adding material to the build-plate 10 to form a portion of each spinal implant constructs 14 adjacent a first end (of each spinal implant construct 14), and then continuing to add the material toward a second end (of each spinal implant construct 14) until each of the spinal implant constructs 14 are formed by the additive manufacturing process. Thereafter, the subtractive manufacturing process or processes can be used to refine the shapes of the spinal implant constructs in order to form the spinal implant S. Furthermore, the subtractive manufacturing process or processes can be used to detach each of the spinal implant constructs 14 from the build-plate 10 along a cut line that forms a leading surface of each of the spinal implants S. These processes are described in U.S. Ser. No. 16/523,079.

The spinal constructs 14 formed on the build-plate 10 are accurately formed with respect to one another on the build-plate 10. However, positioning of the set 12 of the spinal constructs 14 relative to the build-plate 10 can vary. This shifting of the position of the set 12 of constructs 14 relative to a correct position on the build-plate 10 can be caused, for example, by variations in the location of the build-plate 10 relative to a vision system (not shown) including one or more laser or optical scanners (not shown) used with an additive manufacturing platform effectuating the additive manufacturing process. The potential for this unwanted shift must be accounted for when the additive manufacturing processes and/or the subtractive manufacturing processes are applied to the spinal implant constructs 14. The below-discussed physical locating features can serve in accurately positioning the build-plate 10 relative to the vision system and the additive manufacturing platform to inhibit the unwanted shift from occurring. Furthermore, the below-discussed physical locating features can also serve in compensating for the unwanted shift by facilitating adjustment of the additive manufacturing processes and/or the subtractive manufacturing processes to account for the unwanted shift.

A first type of the physical locating features for accurately positioning the build-plate 10 can include physical locating features incorporated into build-plate 10 at known locations prior to the additive manufacturing processes. For example, the build-plate 10 includes an upper surface 16 and a lower surface 18, and can include single or multiple edges, surfaces, recesses (e.g., apertures, holes, or slots), and/or protrusions as the first type of the physical locating features for accurately positioning the build-plate 10. U.S. Ser. No. 16/523,079 describes use of single or multiple edges and surfaces for locating the build-plate 10.

While the build-plate 10 depicted in FIGS. 1, 2, and 5 is hexagonal, the shape of the build-plate 10 is not so limited. The build-plate 10 can have any variety of shapes, and these shapes can be used in accurately positioning the build-plate 10. As depicted in FIG. 1, the build-plate 10 includes first opposed surfaces 20A and 20B, second opposed surfaces 22A and 22B, and third opposed surface 24A and 24B, and at least one of these can be used as the edges or surfaces used for accurately positioning the build-plate 10.

Furthermore, the upper surface 16 and/or the lower surface 18 can include the recesses and/or protrusions for accurately positioning the build-plate 10. As depicted in FIGS. 1 and 3, for example, the upper surface 16 includes an upper first recess 26 and an upper first protrusion 28, and at least one of these can be used to accurately position the build-plate 10. The upper first protrusion 28, for example, can be cylindrical or frusto-conical. Furthermore, as depicted in FIG. 2, for example, the lower surface 18 can include a lower second recess 30 and a lower second protrusion 32, and at least one of these can be used to accurately position the build-plate 10.

The additive manufacturing platform can incorporate an integrally attached or separable first table-top or spacer 40 (FIG. 3) for use with the build-plate. The first table-top/spacer 40 can include complimentary features for engaging the single or multiple edges, surfaces, recesses, and/or protrusions of the build-plate 10 to accurately position the build-plate 10 relative to the vision system and the additive manufacturing platform. To illustrate, the first table-top/spacer 40 can include single or multiple surfaces and edges for complimentarily engaging the first opposed surfaces 20A and 20B, the second opposed surfaces 22A and 22B, and/or the third opposed surface 24A and 24B to facilitate accurate positioning of the build-plate 10 on the first table-top/spacer 40 relative to the vision system and the additive manufacturing platform.

Additionally or alternatively, the first table-top/spacer 40 can include recesses and/or protrusions for complimentarily engaging the recesses and/or protrusions of the build-plate 10. As depicted in FIG. 3, for example, the first table-top/spacer 40 includes an upper surface 42 including a protrusion 44 and a recess 46. When the build-plate 10 is received on the upper surface 42, the protrusion 44 can be received in the lower second recess 30 of the build-plate 10 and/or the lower second protrusion 32 of the build-plate 10 can be received in the recess 46 to provide a mechanical fit to facilitate accurate positioning of the build-plate 10 on the first table-top/spacer 40 relative to the vision system and the additive manufacturing platform.

Additionally or alternatively, one of more fasteners (not shown) can be used to accurately position the build-plate 10. For example, threaded fasteners can be inserted into and through recesses (not shown) formed in the build-plate 10 and into corresponding recesses (not shown) formed in the table-top/spacer 40. Such recesses formed in the build-plate 10 and/or the table-top/spacer 40 can include complimentary threads (not shown) for engaging the one or more fasteners.

Furthermore, additionally or alternatively, the additive manufacturing platform can also incorporate at least one integrally attached or separable clamping arm. As depicted in FIG. 3, a first clamping arm 50 and a second clamping arm 52 are provided. The first clamping arm 50 includes a lower surface 54 and a protrusion 56 formed on the lower surface 54, and the second clamping arm 52 includes a lower surface 60 and a recess 62 formed on the lower surface 60. Like the upper first protrusion 28, the protrusion 56, for example, can be cylindrical or frusto-conical. When the build-plate 10 is received on the upper surface 42, the first clamping arm 50 can be positioned to facilitate engagement of the protrusion 56 into the upper first recess 26 via a mechanical fit, and the second clamping arm 52 can be positioned to facilitate engagement of the upper first protrusion 28 into the recess 62 via a mechanical fit to facilitate accurate positioning of the build-plate 10 on the first table-top/spacer 40 relative to the vision system and the additive manufacturing platform. The first clamping arm 50 and the second clamping arm 52 can have known positions with respect to the vision system and the additive manufacturing platform to facilitate accurate positioning of the build-plate 10 on the first table-top/spacer 40 relative to the vision system and the additive manufacturing platform. Accurately positioning the build-plate 10 serves to inhibit the unwanted shift.

The above-discussed engagement facilitates accurate positioning of the build-plate 10 on the first table-top/spacer 40 and relative to the vision system and the additive manufacturing platform. In similar fashion, a second table-top or spacer for use with the table-top (identical or similar to the table-top/spacer 40) can be integrally attached or separable from a subtractive manufacturing platform used to effectuate the subtractive manufacturing processes, and the second table-top/spacer and the subtractive manufacturing platform can include identical or similar physical locating features to the first table-top/spacer 40 and the additive manufacturing platform to facilitate accurate positioning of the build-plate 10 via mechanical fit. Furthermore, the subtractive manufacturing platform can also include identical or similar clamping arms to the first clamping arm 50 and the second clamping arm 52 for engaging the first type of the physical locating features formed on the build-plate 10 in identical or similar fashion to the first clamping arm 50 and the second clamping arm 52. Thus, the above-discussed engagement can identically or similarly facilitate accurate positioning of the build-plate 10 on the second table-top/spacer and relative to the subtractive manufacturing platform to inhibit the unwanted shift.

The first type of the physical locating features of the build-plate 10 can also be used to compensate for the unwanted shift. To illustrate, the vision system can measure the shift in position of the location of the set 12 of constructs 14 on the build-plate 10 relative to the first type of the physical locating features incorporated into the build-plate 10 such as, for example, the upper first protrusion 28. The vision system can also measure the shift in position of the location of a test pattern and/or test part(s) and/or other fixture(s) formed on the build-plate 10 in addition to the set 12 of the spinal implant constructs 14. Similarly, location probes (identical or similar to the first clamping arm 50 and the second claiming arm 52) can be used to measure the position of the first type of the physical locating features (such as, for example, the upper first protrusion 28), the set 12 of the spinal implant constructs 14, and/or the test pattern and/or test part(s) and/or other fixture(s) to measure the shift in position of the set 12 of the spinal implant constructs 14 and/or the test pattern and/or test part(s) and/or other fixture(s).

For example, x-y coordinates determined along the upper surface 16 of the build-plate 10 of one of the spinal implant constructs 14 relative to the upper first protrusion 28 can be measured, and the closest one and/or the farthest one of the spinal implant constructs 14 can be used for the measurements. These x-y coordinates can be compared to x-y position of a correct position of the set 12 of the spinal implant constructs 14 to quantify a measured amount of the unwanted shift. These measurements then can be used as a part of a correction factor that can be determined/calculated and used to adjust the additive manufacturing processes and/or the subtractive manufacturing processes by adjusting the position of the build-plate 10 relative to the additive manufacturing platform and/or the subtractive manufacturing platform to accurately position the build-plate 10 to account for the unwanted shift.

A second type of the physical locating features for accurately positioning the build-plate 10 can include physical locating features incorporated into the build-plate 10 at known locations with respect to the set 12 of the spinal implant constructs 14 during the additive manufacturing process contemporaneously with the formation of the set 12 of the spinal implant constructs 14. The second type of the physical locating features can be in addition or alternative to the first type of the physical locating features. For example, the build-plate 10 incorporating the second type of the physical locating feature can also include the upper first recess 26, the upper first protrusion 28, the lower second recess 30, and/or the lower second protrusion 32. Furthermore, build-plate 10 incorporating the second type of the physical locating features can use the upper first recess 26, the upper first protrusion 28, the lower second recess 30, and/or the lower second protrusion 32, and the second type of the locating features to the accurately position, as discussed above, the build-plate 10 relative to the additive manufacturing platform and/or the subtractive manufacturing platform.

As depicted in FIG. 5, the second type of the locating features can include a fixture 70 formed on the upper surface 16 during the formation of the set 12 of the spinal implant constructs 14 using the additive manufacturing process. The fixture 70 can be shaped as a ring formed on the upper surface 16 of the build-plate 10 adjacent the spinal implant constructs 14. The fixture 70 includes a recess 72 for facilitating engagement with, for example, the protrusion 56 formed on the first clamping arm 50. Additionally or alternatively, the second type of the locating features can include a protrusion that is identical or similar to the upper first protrusion 28 formed on the upper surface 16 during the formation of the set 12 of the spinal implant constructs 14 using the additive manufacturing process. The recess 62 formed in the second clamping arm 52 can be used to engage the protrusion (identical or similar to the upper first protrusion 28). Furthermore, additionally or alternatively, the second type of the locating features can include the above-discussed test pattern, test part(s), and/or other fixture(s) formed on the upper surface 16 during the formation of the set 12 of the spinal implant constructs 14 using the additive manufacturing process.

Figure 6:
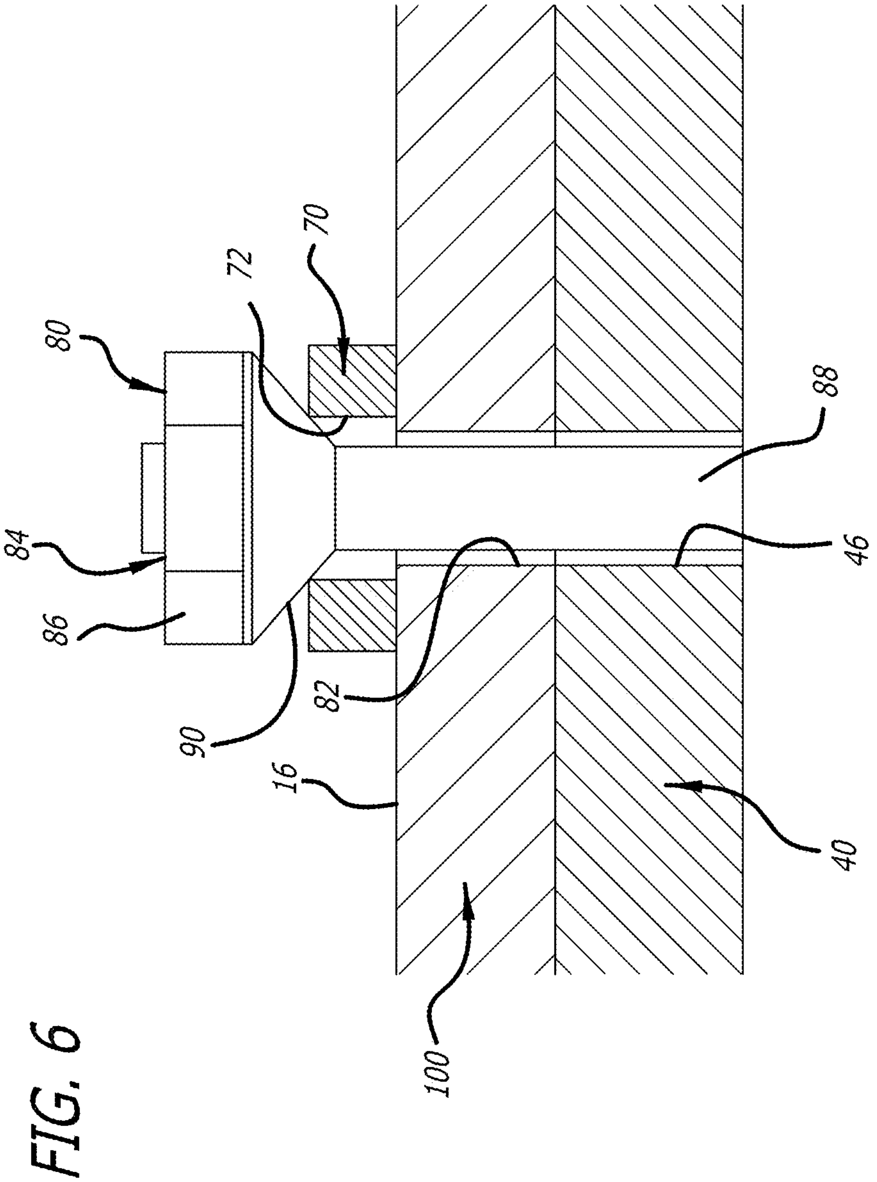
FIG. 6 is a cross-sectional, elevational view of a fastener assembly used in holding the build-plate in position.

Additionally or alternatively, a mechanical fastener assembly 80, as depicted in FIG. 6, can be used with the second type of the locating features to facilitate accurate positioning of the build-plate 10. To illustrate, the fixture 70 can be formed around a recess 82 formed in the build-plate 10. As such, the recess 82 can communicate with the recess 72 formed in the fixture 70, and also communicate with the recess 46 formed in the table-top/spacer 40. The recess 46 formed in the table-top spacer 40 and/or the recess 82 formed in the build-plate 10 can include threads (not shown) for engaging portions of the mechanical fastener assembly 80. Furthermore, the fastener assembly 80 can include a bolt 84 having head 86 and a shaft 88. As depicted in FIG. 6, the head 86 can include a frusto-conical contact surface 90 for contacting the fixture 70, and the shaft 88 can include complimentary threads (not shown) for engaging threads of the recess 46 and/or the recess 82. Furthermore, rather using the bolt 84, the fastener assembly 80 include a rod (not shown) extending through the recess 46 and/or the recess 82, and the recess 72. The rod could include threads (not shown) for engaging the threads (not shown) in the recess 46 and/or the recess 82, and engaging threads of nut (not shown). The nut could also include a surface identical or similar to the frusto-conical contact surface 90. When contacted to a portion of the fixture 70, the frusto-conical contact surface 90 can be used in accurately positioning the build-plate 10. Fasteners similar to the fastener assembly 80 can be used without corresponding use of the fixture 70 to attach the build-plate 10 to the table-top/spacer 40.

The first clamping arm 50 and the second clamping arm 52, as discussed above, can have known positions with the respect to the vision system and the additive manufacturing platform to facilitate accurate positioning of the build-plate 10 on the first table-top/spacer 40 relative to the vision system and the additive manufacturing platform. Furthermore, the subtractive manufacturing platform can also include identical or similar clamping arms to the first clamping arm 50 and the second clamping arm 52 for engaging the second type of the physical locating features formed on the build-plate 10 in identical or similar fashion to the first clamping arm 50 and the second clamping arm 52. Thus, the above-discussed engagement can identically or similarly facilitate accurate positioning of the build-plate 10 on the second table-top/spacer relative to the vision system and the subtractive manufacturing platform.

Use of the fixture 70, the protrusion (identical or similar to the upper first protrusion 28), the test pattern, the test part(s), and/or the other fixture(s) can remove the need to use a correction factor to adjust the position of the build-plate 10 relative to the additive manufacturing platform and/or the subtractive manufacturing platform. Given that, the fixture 70, the protrusion (identical or similar to the upper first protrusion 28), the test pattern, the test part(s), and/or the other fixture(s) are formed with the set 12 of the spinal implant constructs 14, and are fixed in position with respect to one another during the additive manufacturing process, there is limited, if any, amount of the above-discussed unwanted shift. The build-plate 10 can be adjusted relative to the additive manufacturing platform and/or the subtractive manufacturing platform using the second locating features as references to accurately position the build-plate 10. Thus, a correction factor will likely be unnecessary when using the second type of the physical locating features (such as the fixture 70, the protrusion (identical or similar to the upper first protrusion 28)), the test pattern, the test part(s), and/or the other fixture(s) are incorporated into the build-plate 10 at known locations during the additive manufacturing process. However, if necessary, the above-discussed correction factor can be determined/calculated for the second type of the location features and the set 12 of the spinal implant constructs 14.

A third type of the physical locating features for accurately positioning the build-plate 10 can be similar to the second type of the physical locating features. The third type of the physical locating features can initially be formed on the build-plate 10 during by the additive manufacturing process. However, the third type of the physical locating features are formed on the build-plate 10 prior to formation of the set 12 of the spinal implant constructs 14. The initial formation of the third type of the physical locating features allows the relative position of the build-plate 10 to be adjusted before the formation of the set 12 of the spinal implant constructs 14 on the build-plate 10.

Like the second type of the physical locating features, the third type of the physical locating features can include the fixture 70, the protrusion (identical or similar to the upper first protrusion 28), the test pattern, the test part(s), and/or other fixture(s) formed via the additive manufacturing processes on the build-plate 10. The third type of the physical locating features can also be formed via etching on, for example, the upper surface 16 of the build-plate 10.

After formation of the third type of the locating features on the upper surface 16 of the build-plate 10, the third type of the locating features can be used as reference for moving the build-plate 10 relative to the vision system, and/or moving the vision system relative to the build-plate 10 for accurately positioning the build-plate 10 to facilitate application of the additive manufacturing processes. To facilitate use as a reference, the third type of locating features can include one or more fixture(s) that have geometric shapes aiding a determination of x, y, and z position(s) and x, y, and z rotational orientation(s) of the third type of locating features. For example, fixture(s) used as the third type of locating features can include one or more long flat surfaces and/or long straight edges that can be as long as the build-plate 10. The long flat surfaces and/or long straight edges can be used to determine the x, y, and z coordinates of the fixture(s) along the upper surface 16, and determine the rotational orientation of the fixture(s) relative to the x, y, and z axes. The third type of locating features can also include two or more fixtures that are used to determine positions of, orientations of, and distances between the fixture(s). The two or more fixture(s) can be positioned at different ends and/or opposing corners of the build-plate 10. These fixture(s) can also be used as the fixture(s) of the second type of locating features.

The additive manufacturing platform could include a third table-top (not shown) or spacer (not shown) for use with the table-top that is adjustable to move the build-plate 10 relative to the vision system, and/or the vision system could be adjustable relative to the build-plate 10 when using the additive manufacturing platform. For example, the third table-top/spacer could be an x-y adjustment table or part of an x-y adjustment table, and/or the vision system could be moveable via mechanical actuators to facilitate the necessary adjustment. Once the build-plate 10 is accurately positioned, the additive manufacturing process then can be continued to form the set 12 of the spinal implant constructs 14 on the build-plate 10 via use of the additive manufacturing platform.

The adjustment of the build-plate 10 facilitates accurate positioning for the continued use of the additive manufacturing platform. In similar fashion, a subtractive manufacturing platform could include a fourth table-top (not shown) or spacer (not shown) for use with the table-top identical or similar to the third table-top/spacer that is identically or similarly adjustable to facilitate accurate positioning of the build-plate 10 to effectuate the subtractive manufacturing process.

Use of the fixture 70, the protrusion (identical or similar to the upper first protrusion 28), the test pattern, the test part(s), and/or the fixture(s), and use of the third table-top/spacer, the fourth table-top/spacer, and/or the adjustable vision system can remove the need to use a correction factor. The ability to adjust the location of the build-plate 10 using the reference afforded by the third type of the locating features affords accurately positioning during the additive manufacturing process and the subtractive manufacturing process without the need for a correction factor.

While the set 12 of the spinal implant constructs 14 is formed on the build-plate 10, the present disclosure is not so limited. Other devices can be formed on the build-plate 10 using the above-discussed additive manufacturing processes, and then manufactured or machined using the above-discussed subtractive manufacturing processes.

It should be understood that various aspects disclosed herein may be combined in different combinations than the combinations specifically presented in the description and the accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method of using a build-plate comprising:

providing a build-plate having an upper surface, a lower surface, and a first locating feature;

providing an additive manufacturing platform including one of a table-top and a spacer, the one of the table-top and the spacer including an upper surface and a second locating feature;

positioning the build-plate on the upper surface of the one of the table-top and the spacer, and engaging the first locating feature and the second locating feature;

forming on the upper surface of the build-plate a third locating feature and a set of orthopedic implant constructs via an additive manufacturing process performed by the additive manufacturing platform, locations of the third locating feature and the set of the orthopedic implant constructs being known with respect to one another;

measuring a position of the set of the orthopedic implant constructs relative to the third locating feature, and determining, if necessary, a correction factor based on the measured position of the set of orthopedic implant constructs relative to the third locating feature; and using the third locating feature for relative adjustment of the build-plate relative to a subtractive manufacturing platform to facilitate accurate positioning for performance of a subtractive manufacturing process on each of the orthopedic implant constructs.

2. The method of claim 1, further comprising adding material to the upper surface of the build-plate to form a portion of each of the orthopedic implant constructs at and adjacent a first end and continuing to add the material toward a second end until each of the orthopedic implant constructs are formed by the additive manufacturing process.

3. The method of claim 1, wherein each of orthopedic implant constructs is detached from the build-plate along a cut line that forms a surface of a resulting orthopedic implant.

4. The method of claim 1, wherein determining the correction factor includes determining a shift between an accurate position of the set of the orthopedic implant constructs and the measured position of the set of the orthopedic implant constructs.

5. The method of claim 1, further comprising using the correction factor for relative adjustment of the build-plate relative to a subtractive manufacturing platform to facilitate accurate positioning for performance of a subtractive manufacturing process on each of the orthopedic implant constructs.

6. The method of claim 1, wherein engaging the first locating feature and the second locating feature includes forming a mechanical fit.

7. The method of claim 6, further comprising clamping the build-plate to the one of the table-top and the spacer using a clamping arm engaged to the third locating feature.

* * * * *